(12) United States Patent
Hamada et al.

(10) Patent No.: US 8,222,216 B2
(45) Date of Patent: Jul. 17, 2012

(54) MESENCHYMAL CELL PROLIFERATION PROMOTER AND SKELETAL SYSTEM BIOMATERIAL

(75) Inventors: Yoshinosuke Hamada, Suita (JP); Nariaki Matsuura, Suita (JP); Hiroshi Egusa, Suita (JP); Yoshitoshi Kaneda, Suita (JP); Masayuki Okazaki, Hiroshima (JP)

(73) Assignees: Osaka University, Suita-Shi (JP); Hiroshima University, Higashi-Hiroshima-Shi (JP)

( * ) Notice: Subject to any disclaimer, the term of this patent is extended or adjusted under 35 U.S.C. 154(b) by 595 days.

(21) Appl. No.: 12/310,577

(22) PCT Filed: Aug. 29, 2007

(86) PCT No.: PCT/JP2007/066756
§ 371 (c)(1),
(2), (4) Date: Feb. 27, 2009

(87) PCT Pub. No.: WO2008/026634
PCT Pub. Date: Mar. 6, 2008

(65) Prior Publication Data
US 2011/0245187 A1    Oct. 6, 2011

(30) Foreign Application Priority Data
Aug. 31, 2006  (JP) ................. 2006-236970

(51) Int. Cl.
*A61K 38/08* (2006.01)
*C07K 7/06* (2006.01)
(52) U.S. Cl. .................. 514/21.7; 514/1.1; 530/327
(58) Field of Classification Search .................. None
See application file for complete search history.

(56) References Cited

U.S. PATENT DOCUMENTS

| 2004/0266696 A1 | 12/2004 | Nokihara et al. |
| 2006/0105013 A1* | 5/2006 | Ashkar et al. ................. 424/423 |

FOREIGN PATENT DOCUMENTS

| EP | 1452182 | 9/2004 |
| WO | WO-99/08730 | 2/1999 |
| WO | WO 02/32940 | 4/2002 |
| WO | WO-03/047645 | 6/2003 |
| WO | WO-2005/094865 A1 | 10/2005 |
| WO | WO-2005/094912 | 10/2005 |

OTHER PUBLICATIONS

Form PCT/ISA/210 Re: PCT/JP2007/066756.
Form PCT/IPEA/409 Re: PCT/JP2007/066756.
Okazaki M, Ohmae H, Hino T, Insolubilization of apatite-collagen composites by UV irradiation. Biomaterials 1989; 10:564-568.
Okazaki M, Ohmae H, Takahashi J, Kimura H, Sakuda M. Insolubilized properties of UV-irridiated CO3apatite-collagen composites. Biomaterials 1990; 11: 568-572.
Itoh M, Shimazu A, Hirata I, Yoshida Y, Shintani H, Okazaki M. Characterization of CO3Ap-collagen sponges using x-ray high-resolution microtomography. Biomaterials 2004; 25: 2577-2583.
Yokosaki Y, Matsuura N, Sasaki T, Murakami I, Schneider H, Higashiyama S, Saitoh Y, Yamakido M, Taooka Y, Sheppard D. The integrin a9b1 binds to a novel recognition sequence (SVVYGLR) in the thrombin-cleaved amino-terminal fragment of osteopontin, J. Biol Chem 1999; 274: 36328-36334.
Hamada Y, Nokihara K, Okazaki M, Fujitani W, Matsumoto T, Matsuo M. Umakoshi Y, Takahashi J, Matsuura N. Angiogenic activity of osteopontin- derived peptide SVVTGLR. Biochem Biophys Res Commun 2003; 310: 153-157.
Hamada Y, Yuki K, Okazaki M, Fujitani W., Matsumoto T, Kobashi Hashida M, Harutsugu K, Nokihara K, Daito M, Matsuura N, Takahashi J. Osetpontin-derived peptide SVVYGLR induces angiogenesis in vivo. Dent Mater J 2004; 23: 650-655.
Schofield K, et al., The Effect of a4β1-Integrin Binding Sequences of Fibronectin on Growth of Cells From Human Hematopoietic Progenitors. Blood, May 1, 1998, vol. 91, No. 9 p. 3230-3238.
Barry S, et al. Analysis of the a4β1 Integrin-Osteopontin Interaction. Experimental Cell Research, 2000, vol. 258, No. 2, p. 342-351.
Bayless K, et al. Identification of Dual a4β1 Integrin Binding Sites within a 38 Amino Acid Domain in the N-terminal Thrombin Fragment of Human Osteopontin. Journal of Biological Chemistry, 2001, vol. 276, No. 16, p. 13483-13489.
Green P. et al., Structural elements of the Osteopontin SVVYGLR motif important for the interaction with a4 integrins. FEBS Letter, 2001, vol. 503, No. 1, p. 75-79.
Shin H. et al., Attachment, Proliferation, and migration of marrow stromal osteoblasts cultured on biomimetic Hydrogels Modified with an Osteopontin-Derived Peptide. Biomaterials, 2004, vol. 25, No. 5, p. 895-906.
Shin H. et al., Modulation of differentiation and mineralization of marrow stromal cells cultured on Biomimetic Hydrogels Modified with ARG-GLY-ASP Containing Peptides. Journal of Biomedical Materials Research Part A., 2004, vol. 69, No. 3, p. 535-543.
Office Action from Japanese Patent Application No. 2008-532088, mailed on Jan. 17, 2012.

* cited by examiner

*Primary Examiner* — Julie Ha
(74) *Attorney, Agent, or Firm* — Edwards Wildman Palmer LLP; David G. Conlin; Elizabeth Spar

(57) ABSTRACT

It is found that a SVVYGLR peptide (SEQ ID NO: 1) can promote proliferation of mesenchymal cells such as marrow-derived mesenchymal stem cells and dental pulp cells. A carbonate apatite-collagen sponge containing the SVVYGLR peptide (SEQ ID NO: 1) is useful as a biomaterial for the regeneration of bone marrow or dental pulp. It becomes possible to provide a skeletal system biomaterial which is capable of promoting the proliferation of the mesenchymal cells and is useful as artificial bone marrow or artificial dental pulp for repairing a defect in a bone marrow tissue or a dental pulp tissue.

1 Claim, 8 Drawing Sheets

FIG.6
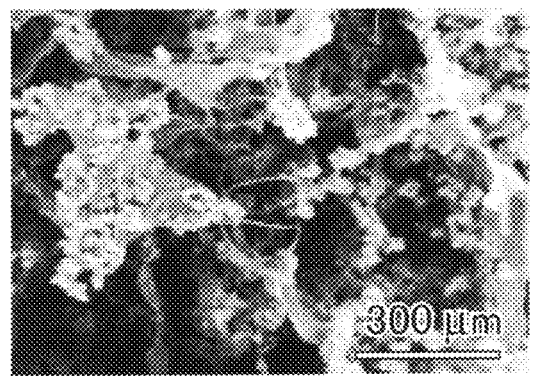
(a)
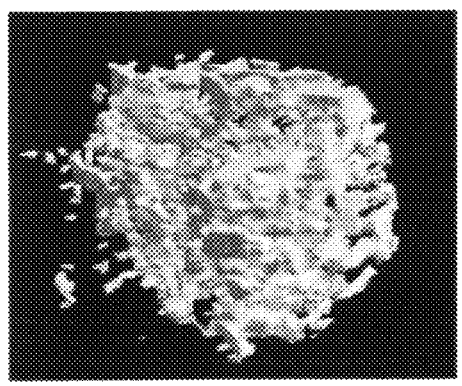
(b)

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Ser Val Val Tyr Gly Leu Arg
1               5
```

MESENCHYMAL CELL PROLIFERATION PROMOTER AND SKELETAL SYSTEM BIOMATERIAL

SEQUENCE LISTING

The instant application contains a Sequence Listing which has been submitted in ASCII format via EFS-Web and is hereby incorporated by reference in its entirety. Said ASCII copy, created on Sep. 29, 2010, is named 83585709.txt and is 670 bytes in size.

TECHNICAL FIELD

The present invention relates to a mesenchymal cell proliferation promoter and a skeletal system biomaterial containing the mesenchymal cell proliferation promoter.

BACKGROUND ART

In this aging society, it is desired to develop a technique for rebuilding deficits and injuries on such tissues as bones and teeth. Progress in regeneration medicine arouses an interest especially toward a skeletal system biomaterial. As a revolutionary technique for repairing lost tissues, it is desired to develop artificial bone marrow and artificial dental pulp that are components of hard tissues.

Especially in the dentistry field, a medical treatment for preserving dental pulp tissues is increasingly becoming important since it is desirable to live with own teeth as long as possible. Dental pulp is centrally located in a tooth, and comprises ground substance, blood vessel, and nerve. In the case in which the tooth was affected with caries and the affection spread to a part of the dental pulp, a useful treatment that is gathering attention is a vital pulpectomy, in which only a site of infection is locally severed and rest of the dental pulp is preserved.

However, in reality, appropriately treating a severed surface of the dental pulp is technically difficult, and it is not always promising to keep the severed dental pulp in good condition. Therefore, it is desired to establish a least-invasive treatment method for more appropriately treating the dental pulp. In this situation, if a deficit on the dental pulp due to excision of an affected site can be restored to an original state and the dental pulp tissue can be preserved, this may significantly contribute to improvement in people's QOL and reduction of medical cost.

Various types of skeletal system biomaterials for repairing defects in bone tissues have been studied from a viewpoint of biodegradability of a carbonate apatite ($CO_3Ap$). The inventors propose use of a carbonate apatite-collagen complex as a biomaterial. The carbonate apatite-collagen complex is produced from the carbonate apatite and a collagen, which are similar to a living hard tissue in terms of chemical composition and crystallinity degree (See non-patent document 1 and non-patent document 2). The carbonate apatite-collagen complex showed a good biocompatibility when inserted into abdomen or under pericranium of a rat.

However, an inner bulk of the carbonate apatite-collagen complex has no room for cells to infiltrate into. It was found that when use of a sponge-like carbonate apatite-collagen complex provides large pores, proliferation of osteoblasts and infiltration of cells into the pores were promoted (See non-patent document 3).

In order for the biomaterial to survive after regeneration of a lost tissue so that the biomaterial fully exercises its function, it is essential to provide oxygen and nutrients to cells. That is, blood vessels for giving hybrid functions to the skeletal system biomaterial is necessary for maintenance and growth of bones.

As described above, the carbonate apatite-collagen complex shows appropriate biocompatibility, and the sponge-like material of the complex includes enough room for the cells to infiltrate into. However, even if the cells were infiltrated into the sponge-like material, the cells would not be able to survive without the blood vessels that provide oxygen and nutrients. Therefore, angiogenesis inside the biomaterial is essential.

A process of angiogenesis is started with digesting blood vessel basement membrane with endothelial cells. After that, the cells move and proliferate to form a canal structure. It is reported by many researchers that the cellular reactions are rigorously controlled by a signal emitted from such factors as various growth factors and a cytokine (vessel endothelial growth factor (VEGF), fibroblast growth factor (FGF), and interleukin 8).

An osteopontin (OPN), which is an extracellular matrix protein, is a protein phosphate containing a large amount of sialic acid, and is widely distributed in bones, kidney, brain, skin, and the like. The OPN relates to bone metabolism, and intermediates an inflammation reaction and the angiogenesis. Recently, an amino-acid sequence [Ser-Val-Val-Tyr-Gly-Leu-Arg (SVVYGLR)] (SEQ ID NO: 1) relating to an angiogenic action has been found in the OPN (See patent document 1, non-patent document 4, and non-patent document 5). The SVVYGLR (SEQ ID NO: 1), which adjacents to an RGD sequence within a molecule of the osteopontin, was being exposed by thrombin cleavage, so this motif is believed to play an important role in a clinical condition. We have already succeeded in artificially composing the sequence of SVVYGLR (SEQ ID NO: 1) as a blood vessel growth factor (See non-patent document 6).

PATENT DOCUMENT 1

International Patent Publication WO2003/030925

NON-PATENT DOCUMENT 1

Okazaki M, Ohmae H, Hino T. Insolubilization of apatite-collagen composites by UV irradiation. Biomaterials 1989; 10: 564-568.

NON-PATENT DOCUMENT 2

Okazaki M, Ohmae H, Takahashi J, Kimura H, Sakuda M. Insolubilized properties of UV-irradiated $CO_3$apatite-collagen composites. Biomaterials 1990; 11: 568-572.

NON-PATENT DOCUMENT 3

Itoh M, Shimazu A, Hirata I, Yoshida Y, Shintani, H, Okazaki M. Characterization of $CO_3$Ap-collagen sponges using x-ray high-resolution microtomography. Biomaterials 2004; 25: 2577-2583.

NON-PATENT DOCUMENT 4

Yokosaki Y, Matsuura N, Sasaki T, Murakami I, Schneider H, Higashiyama S, Saitoh Y, Yamakido M, Taooka Y, Sheppard D. The integrin a9b1 bind to a novel recognition sequence (SVVYGLR) (SEQ ID NO: 1) in the thrombin-cleaved amino-terminal fragment of osteopontin. J Biol Chem 1999; 274: 36328-36334.

NON-PATENT DOCUMENT 5

Hamada Y, Nokihara K, Okazaki M, Fujitani W, Matsumoto T, Matsuo M, Umakoshi Y, Takahashi J, Matsuura N. Angiogenic activity of osteopontin-derived peptide SVVYGLR (SEQ ID NO: 1). Biochem Biophys Res Commun 2003; 310: 153-157.

NON-PATENT DOCUMENT 6

Hamada Y, Yuki K, Okazaki M, Fujitani W, Matsumoto T, Kobayashi Hashida M, Harutsugu K, Nokihara K, Daito M, Matsuura N, Takahashi J. Osetpontin-derived peptide SVVYGLR (SEQ ID NO: 1) induces angiogenesis in vivo. Dent Mater J 2004; 23: 650-655.

DISCLOSURE OF INVENTION

As described above, in order for the function of the biomaterial to be fully exercised so as to repair the lost tissue, the important things are not only to regenerate the lost tissue and keep the biomaterial survive, but also to perform the angiogenesis in the regenerated tissue. However, in order to be applied as a biomaterial for promoting regeneration of the bone marrow tissue and dental pulp tissue, the biomaterial is preferably further capable of promoting proliferation of mesenchymal cells that constitute intercellular substrates.

The present invention is made to solve the above problem, and an object of the present invention is to provide a skeletal system biomaterial including a function of promoting proliferation of the mesenchymal cells.

The inventors have diligently worked to solve the above problem, and newly found that a SVVYGLR peptide (SEQ ID NO: 1), which is known for relating to the angiogenic action, has a function to promote proliferation of such mesenchymal cells as marrow-derived mesenchymal stem cells and dental pulp cells. The inventors have also found that a carbonate-apatite collagen sponge containing the SVVYGLR peptide (SEQ ID NO: 1) is useful as the biomaterial for regenerating bone marrow, because blood vessels are formed in a sponge area and the mesenchymal cells are infiltrated into the sponge when the carbonate apatite-collagen sponge containing the SVVYGLR peptide (SEQ ID NO: 1) is implanted into a lost bone marrow. The present invention was made based on these findings.

That is, a mesenchymal cell proliferation promoter according to the present invention is a peptide comprising an amino-acid sequence shown in SEQ. ID. NO: 1 as an active ingredient.

A skeletal system biomaterial according to the present invention comprises an angiogenic inducement and mesenchymal cell proliferation promoter according to the present invention. The skeletal system biomaterial is preferably a sponge-like material formed from a complex of a carbonate apatite and a collagen. Further, the skeletal system biomaterial preferably contains a mesenchymal cell adhesion promoter containing the peptide comprising the amino-acid sequence shown in SEQ. ID. NO: 1 as the active ingredient.

A method according to the present invention for regenerating a bone marrow tissue or dental pulp tissue uses the skeletal system biomaterial according to the present invention.

Additional objects, features, and strengths of the present invention will be made clear by the description below. Further, the advantages of the present invention will be evident from the following explanation in reference to the drawings.

Figure 3:
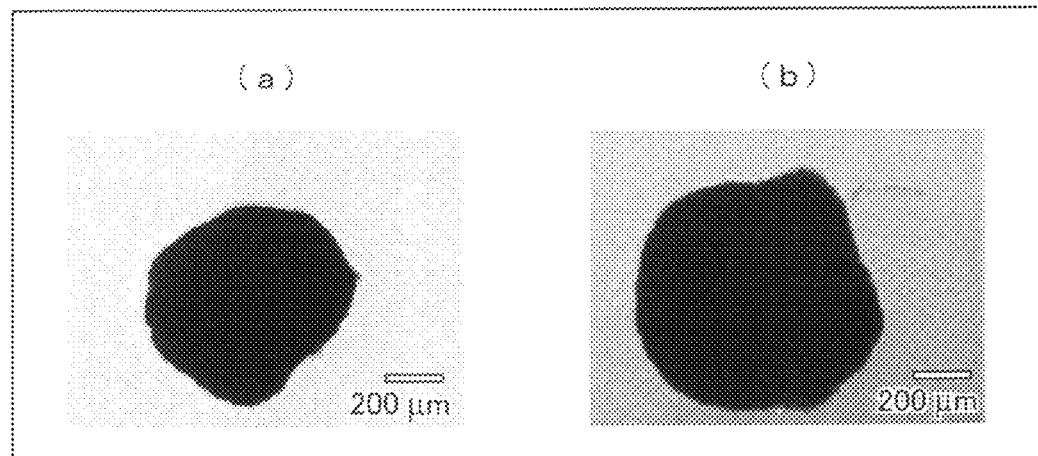

(a) of FIG. 3 is a phase contrast microscope image of a mesenchymal cell pellet, in which no SVVYGLR peptide (SEQ ID NO: 1) is added to a culture medium. (b) of FIG. 3 is a phase contrast microscope image of a mesenchymal cell pellet, in which the SVVYGLR peptide (SEQ ID NO: 1) is added to a culture medium.

Figure 4:
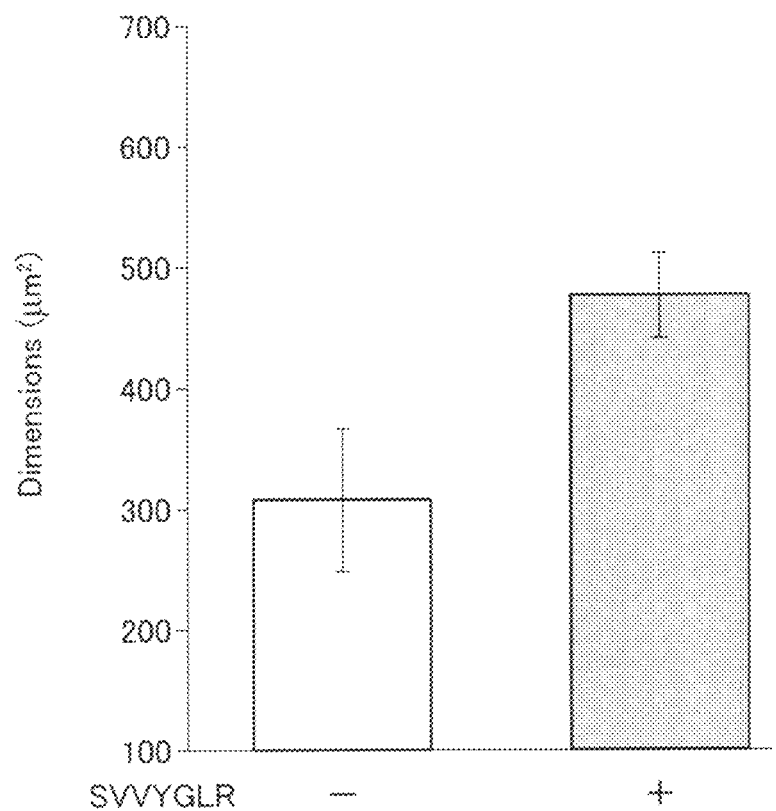

FIG. 4 is a graph showing numerical values of planar dimensions (μm2) of the pellet in the phase contrast microscope image, the planar dimensions being measured by using an image analysis software. FIG. 4 discloses "SVVYGLR" as SEQ ID NO: 1.

Figure 5:
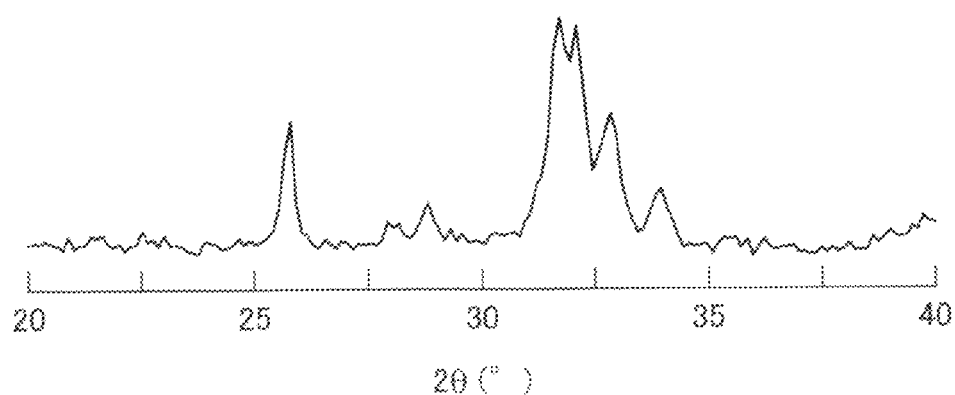

FIG. 5 is a chart showing an X-ray diffraction pattern of a synthetic carbonate apatite.

(a) of FIG. 6 is a scanning electron micrograph of a carbonate apatite-collagen sponge. (b) of FIG. 6 is a three-dimensional image of the carbonate apatite-collagen sponge extracted by using an X-ray microcomputer laminagraphy.

Figure 7:
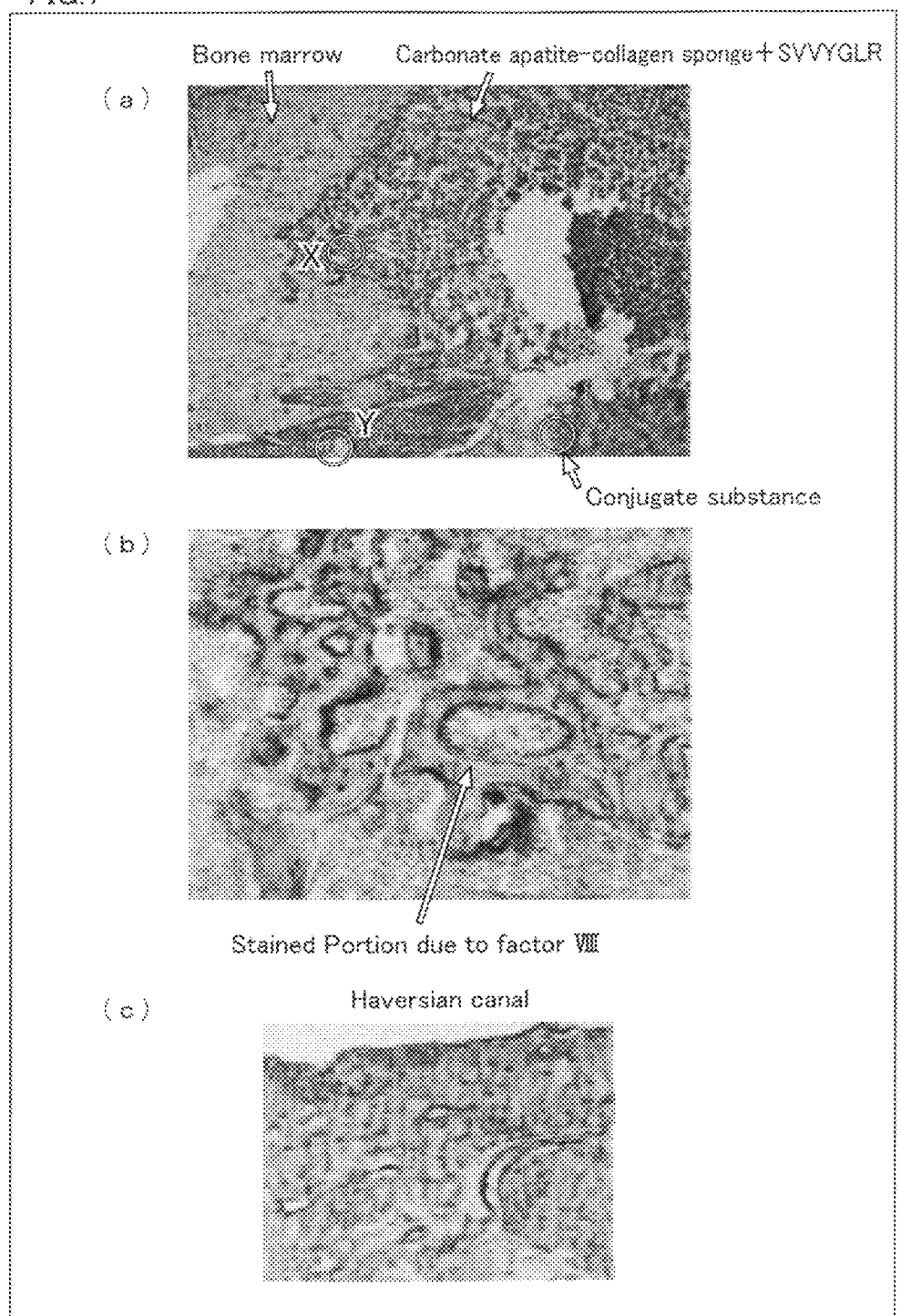

FIG. 7 is a histological picture of a graft to which the carbonate apatite-collagen sponge containing the SVVYGLR peptide (SEQ ID NO: 1) is implanted. (a) of FIG. 7 is a histological picture of low magnification, (b) of FIG. 7 is a strong enlarged image of X part in (a) of FIG. 7, and (c) of FIG. 7 is a strong enlarged image of Y part in (a) of FIG. 7.

Figure 8:
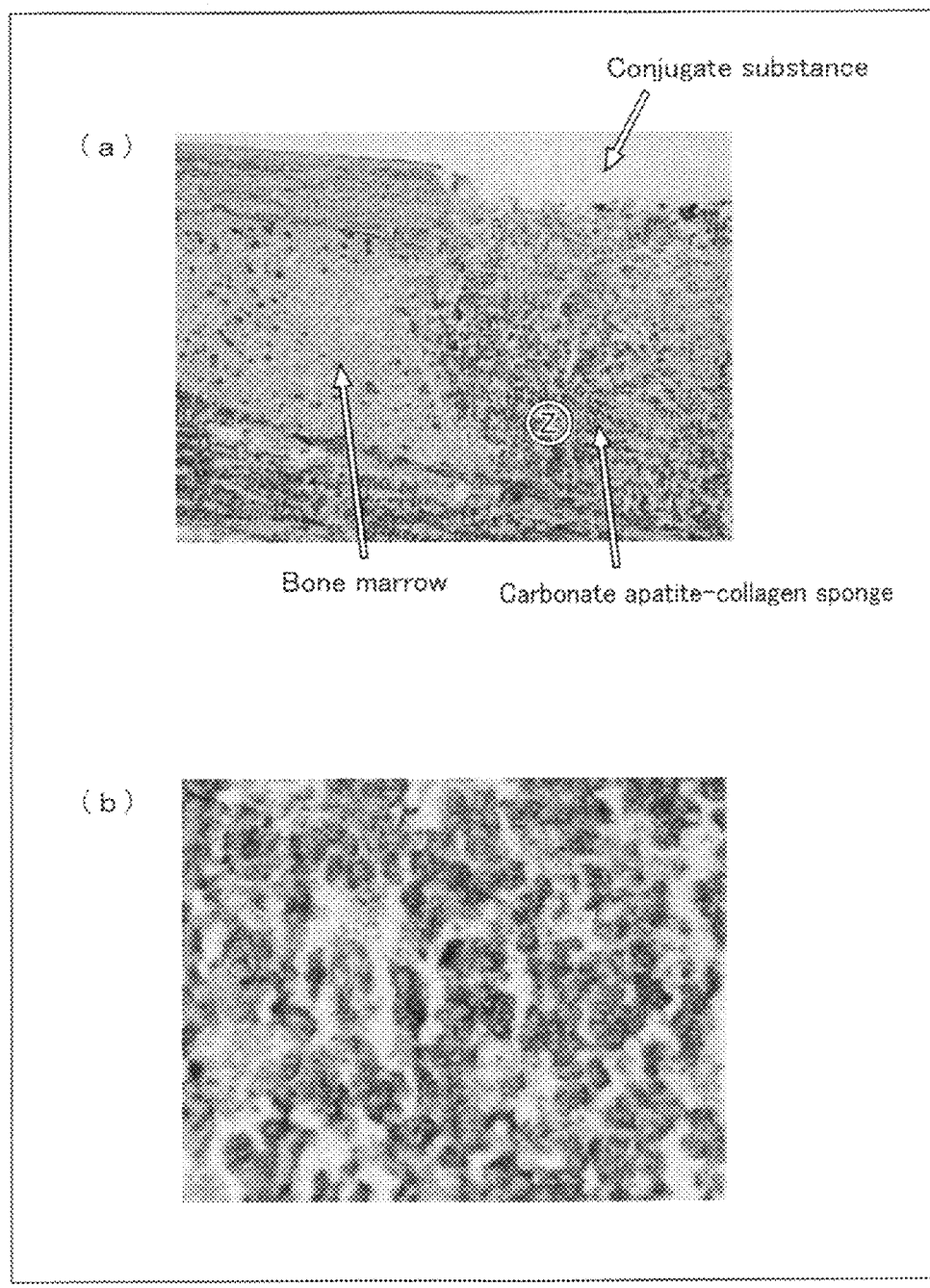

FIG. 8 is a histological picture of a graft to which the carbonate apatite-collagen sponge containing no SVVYGLR peptide (SEQ ID NO: 1) is implanted. (a) of FIG. 8 is a histological picture of low magnification, and (b) of FIG. 8 is a strong enlarged image of Z part in (a) of FIG. 8.

Figure 9:
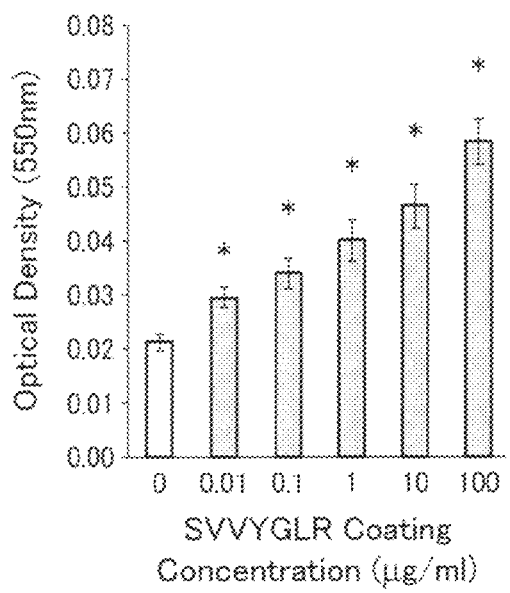

FIG. 9 is a graph showing counts of the number of human marrow-derived mesenchymal stem cells adhered to a plate coated with the SVVYGLR peptide (SEQ ID NO: 1).

Figure 10:
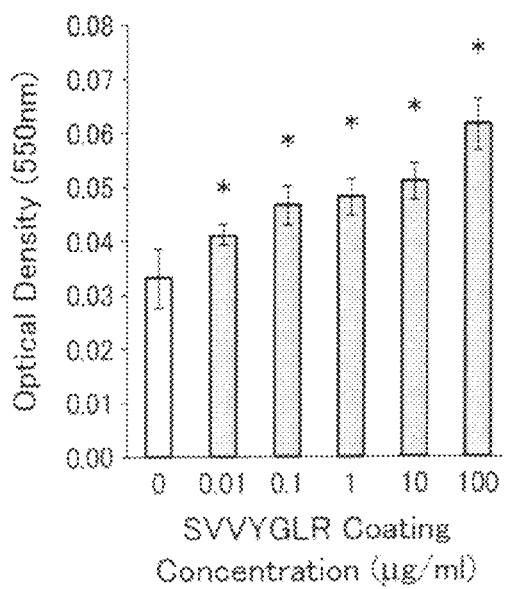

FIG. 10 is a graph showing counts of the number of human gingival fibroblasts adhered to the plate coated with the SVVYGLR peptide (SEQ ID NO: 1).

Figure 11:
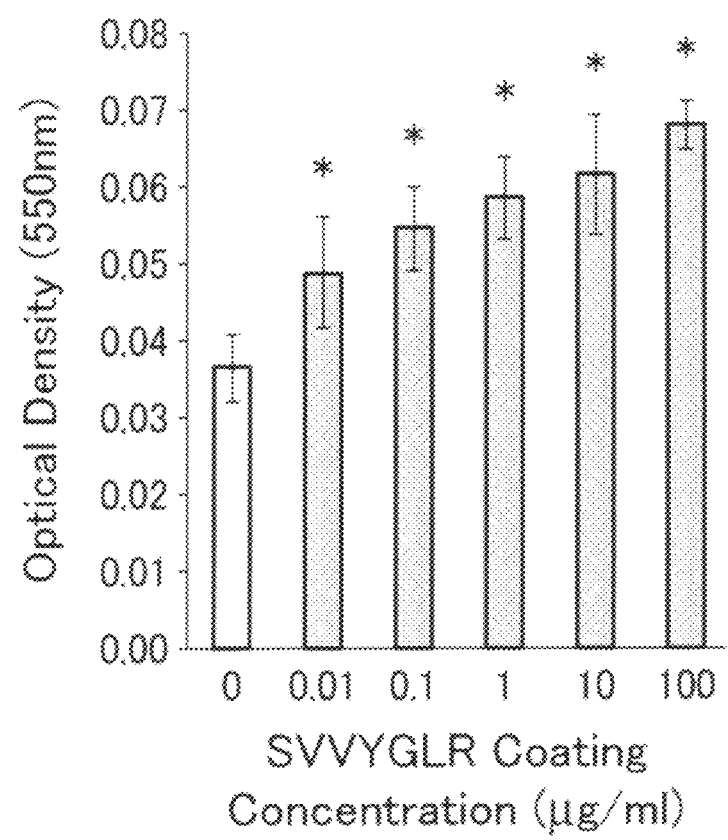

FIG. 11 is a graph showing counts of the number of periodontal ligament cells adhered to the plate coated with the SVVYGLR peptide (SEQ ID NO: 1).

BEST MODE FOR CARRYING OUT THE INVENTION

[Mesenchymal Cell Proliferation Promoter]

A mesenchymal cell proliferation promoter according to the present invention may be selected from those containing a peptide as an active ingredient, the peptide comprising an amino-sequence shown in SEQ. ID. NO: 1, i.e., seven amino acids of Ser-Val-Val-Tyr-Gly-Leu-Arg (SVVYGLR) (hereinafter called "SVVYGLR peptide") (SEQ ID NO: 1). The SVVYGLR peptide (SEQ ID NO: 1) is publicly known as a peptide having an angiogenic action and as a peptide that is present in an osteopontin. But as described in the following examples, the inventors have confirmed that the SVVYGLR peptide (SEQ ID NO: 1) has a proliferation-promoting activity on mesenchymal cells and therefore the SVVYGLR peptide (SEQ ID NO: 1) can act as an active ingredient of the mesenchymal cell proliferation promoter.

The mesenchymal cell proliferation promoter according to the present invention may also be selected from those containing a peptide as the active ingredient, the peptide being the SVVYGLR peptide (SEQ ID NO: 1) in which one or several amino acids are deleted, substituted, or added, provided that the mesenchymal cell proliferation promoter has a proliferation-promoting activity on the mesenchymal cells.

The above described "one or several amino acids are deleted, substituted, or added" means deletion, substitution, or addition of one or several amino acids (preferably three, more preferably two, most preferably one amino acid) that can be performed by publicly known peptide mutation methods such as a site-directed mutagenesis. Such mutant peptide is not limited to those artificially mutated with publicly known peptide mutation methods, but may be selected from those isolated and purified from naturally occurring peptides.

The mutants preferably include substitution, deletion, or addition of amino acid(s), either conservatively or non-conservatively. Especially preferable among these are silent substitution, addition and deletion, and most preferable is the conservative substitution. These mutants do not alter a peptide activity according to the present invention.

Further, the peptide, which acts as the active ingredient of the mesenchymal cell proliferation promoter according to the present invention, may be selected from SVVYGLR peptides (SEQ ID NO: 1) containing an additional peptide, provided that the peptide has the proliferation-promoting activity on the mesenchymal cells. The additional peptide is not particularly limited, but may be an epitope-labeled peptide such as Arg-tag, His-tag, Myc, or Flag.

Whether the peptide has the proliferation-promoting activity on the mesenchymal cells or not can be checked by comparing a proliferation profile of the mesenchymal cells cultured in a culture solution with the peptide added therein, to that of the mesenchymal cells cultured in a culture solution with no peptide added therein.

Further, by a standard method known in the art, the peptide can be easily synthesized by using a commercially available peptide synthesizing machine. Specifically, the peptide can be synthesized with such a method as a high-efficient solid-phase method of Fmoc chemistry. The peptide can also be produced gene-technologically with a standard method known in the art. The obtained peptide can be confirmed as a desired peptide through HPLC or LCMS etc., by checking for a mass theoretical figure and presence of a single peak or the like.

The mesenchymal cells are cells that constitute connective tissues such as bone marrow and dental pulp, and encompass mesenchymal stem cells that can be differentiated into hard tissue system cells.

The SVVYGLR peptide (SEQ ID NO: 1) can be locally administered alone or in the form of injection solution (the solution made by resolving the peptide in an appropriate solvent such as physiological buffer solution), to a tissue in which an angiogenic inducement and proliferation of the mesenchymal cells are desired. By locally administering the mesenchymal cell proliferation promoter of the present invention to a surrounding area of a wound or the like caused by operation or external injury with such methods as injection, application, or nebulization, the proliferation of the mesenchymal cells is promoted, whereby healing of the wound is promoted. A concentration of the peptide in peptide solution that is used for injection, application, or nebulization is not particularly limited, but generally, approximately 0.001 to 10 μg/mL. Also, a given dose of the peptide solution can be determined as needed depending on a size or depth of the wound or the like, but is preferably as much as covering a whole wound. Further, the peptide solution can be administered once or several times a day everyday or every few days, until the wound is healed. Furthermore, the injection solution may contain another ingredient such as a disinfectant, antiphlogistic analgetic, and/or the like, which is usually contained in curative drugs for wounds.

Moreover, it is also possible to promote the proliferation of the mesenchymal cells by binding the SVVYGLR peptide (SEQ ID NO: 1) to a career and inserting the SVVYGLR peptide-bound (SEQ ID NO: 1) career into a living organism. In this method, since the SVVYGLR peptide (SEQ ID NO: 1) is immobilized to the career, an action of the SVVYGLR peptide (SEQ ID NO: 1) can be selectively exercised on a site to be treated. As a result, the method has a potential as a new DDS (drug delivery system). By locally administering the mesenchymal cell proliferation promoter of the present invention to a site of biomaterial transplantation with such methods as application or nebulization, the proliferation of the mesenchymal cells is promoted, whereby postoperative healing is promoted. The career is not limited to a particular kind, and may be such a material as resin used for bone substitute, teeth substitute, artificial organ or the like, or a biomacromolecule such as a protein. By binding the peptide to the resin, it becomes possible to promote the proliferation of the mesenchymal cells in the tissue around the resin when the resin is inserted into the living organism. Further, it is more preferable to use the protein as the career.

The protein that is used as the career may be selected from any biocompatible proteins, and especially a cell-adhesive protein is preferable for achieving better conjugation with a living tissue. Preferable examples of the cell-adhesive proteins encompass a collagen (gelatin), fibronectin, vitronectin, laminin, and partial hydrolysates of these proteins. However, the present invention is not limited thereto. In terms of preventing allergen reaction, these proteins are preferably purified proteins, from which an allergen was removed.

An amount of the peptide that is bound to the career is not particularly limited and can be determined as needed, but a weight ratio of the career to the peptide (career:peptide) is generally approximately 100:1 to 1:1, preferably approximately 20:1 to 5:1.

The career and the peptide are preferably bound covalently. The career and the peptide can be easily bound, for example, in such a manner that an N-terminal amino group of the peptide is bound to any amino group in the career by using a binding and cross-linking agent such as glutaraldehyde. Further, in the case in which the peptide is to be bound to the resin such as artificial organ, a monomer (the monomer containing a group (e.g., amino group) that can be used in binding with the peptide) may be copolymerized to the resin in advance, so that the group in the resin and the N-terminal amino group of the peptide can be bound. Furthermore, it is also preferable to employ a SVVYGLR peptide (SEQ ID NO: 1) having an end or both ends thereof bound to the other peptide including any amino-acid sequence, so that the other peptide is used for binding to the career.

The SVVYGLR peptide-bound (SEQ ID NO: 1) career can be inserted into the living organism as it is, in addition to the methods of application and nebulization. In the case in which the cell-adhesive protein is employed as the career, the SVVYGLR peptide-bound (SEQ ID NO: 1) career can be used alone or in combination with the other medicinal properties, as a suture thread, as a variety of materials for plastic surgery, and as an adhesion promoter for wounds.

[Mesenchymal Cell Adhesion Promoter]

A mesenchymal cell adhesion promoter according to the present invention may be selected from those containing a peptide as an active ingredient, the peptide comprising an amino-acid sequence shown in SEQ. ID. NO: 1, i.e., seven amino acids of Ser-Val-Val-Tyr-Gly-Leu-Arg (SVVYGLR) (hereinafter called "SVVYGLR peptide") (SEQ ID NO: 1). As described in the following examples, the inventors have confirmed that the SVVYGLR peptide (SEQ ID NO: 1) has an adhesion-promoting activity on mesenchymal cells, and found that the peptide can act as an active ingredient of the mesenchymal cell adhesion promoter.

The mesenchymal cell adhesion promoter according to the invention may also be selected from those containing a peptide as the active ingredient, the peptide being the SVVYGLR peptide (SEQ ID NO: 1) in which one or several amino acids are deleted, substituted, or added, provided the mesenchymal cell adhesion promoter has an adhesion-promoting activity on the mesenchymal cells. Further, the peptide, which acts as the active ingredient of the mesenchymal cell adhesion promoter according to the present invention, may be selected from SVVYGLR peptides (SEQ ID NO: 1) containing an additional peptide, provided the peptide has the adhesion-promoting activity on the mesenchymal cells. The additional peptide is not particularly limited, but may be an epitope-labeled peptide such as Arg-tag, His-tag, Myc, or Flag. A person skilled in the art can easily check whether the peptide has the adhesion-promoting activity on the mesenchymal cells, based on the method set forth in the description. Further, the peptide can be synthesized with one of the methods described above.

The SVVYGLR peptide (SEQ ID NO: 1) can be locally administered alone or in the form of injection solution (the solution made by resolving the peptide in an appropriate solvent such as physiological buffer solution), to a tissue in which adhesion of the mesenchymal cells is desired. By locally administering the mesenchymal cell adhesion promoter of the present invention to a surrounding area of a wound or the like caused by operation or external injury with such methods as injection, application, or nebulization, adhesion of the mesenchymal cells is promoted, whereby healing of the wound is promoted. A concentration of the peptide in peptide solution that is used for injection, application, or nebulization is the same as that described in the section of MESENCHYMAL CELL PROLIFERATION PROMOTER.

Furthermore, it is also possible to promote the adhesion of the mesenchymal cells by binding the SVVYGLR peptide (SEQ ID NO: 1) to a career and inserting the SVVYGLR peptide-bound (SEQ ID NO: 1) career into a living organism. By locally administering the mesenchymal cell adhesion promoter of the present invention to a site of biomaterial transplantation with such methods as application or nebulization, the adhesion of the mesenchymal cells is promoted, whereby postoperative healing is promoted. A preferable material for the career, a preferable amount of the peptide to be bound to the career, and an example of use of the career are the same as those described in the section of MESENCHYMAL CELL PROLIFERATION PROMOTER.

[Skeletal System Biomaterial]

A skeletal system biomaterial of the present invention may be selected from those containing a mesenchymal cell proliferation promoter according to the present invention. Therefore, a publicly known skeletal system biomaterial to which a SVVYGLR peptide (SEQ ID NO: 1) is bound in an appropriate manner is preferable as the skeletal system biomaterial according to the present invention. The most preferable among these is a SVVYGLR peptide-bound (SEQ ID NO: 1) sponge-like skeletal system biomaterial formed from a complex of a carbonate apatite and collagen.

Moreover, the skeletal system biomaterial according to the present invention may further contain a mesenchymal cell adhesion promoter according to the present invention. In this case, the SVVYGLR peptide (SEQ ID NO: 1) acts not only as an active ingredient of the mesenchymal cell proliferation promoter, but also as an active ingredient of the mesenchymal cell adhesion promoter. Thus, the SVVYGLR-bound (SEQ ID NO: 1) skeletal system biomaterial has a proliferation action on the mesenchymal cells as well as an adhesion-promoting activity on the mesenchymal cells.

The sponge-like skeletal system biomaterial formed from the complex of the carbonate apatite and collagen can be produced with the following method, for example.

The carbonate apatite to be used is represented by a general formula of $Ca_{10-X}(PO_4)_{6-Y}(CO_3)_Y(OH)_{2-Z}$, wherein $0 \leq X \leq 3$ to 5, $0 \leq Y \leq 2$ to 4, and $0 \leq Z \leq 1$ to 2. A synthesis method of the carbonate apatite and the carbonate apatite are reported in various papers (e.g., non-patent document 2). For example, the inventors synthesized the carbonate apatite with a method described in example 3 set forth below.

The collagen to be used is not particularly limited, and may be any of commercially available collagens. However, those having low purity, containing an allergen, or having poor quality reproducibility are not preferable for a clinical application. A partially hydrolyzed animal-derived collagen (gelatin), from which the allergen was removed, is commercially available for clinical use, so it is preferable to use such purified collagen or a partial hydrolysate of such collagen.

A sponge-like material can be produced through the steps of: resolving the collagen into acid aqueous solution (e.g., hydrochloric acid solution and phosphating solution), mixing the collagen solution and the carbonate apatite, and freeze-drying the mixture. The collagen solution is to be neutralized (e.g., neutralized by adding NaOH aqueous solution) before or after the carbonate apatite is mixed, so that pH of the solution is preferably within a range of 7 to 9. A ratio of the carbonate apatite is generally 0.001 to 0.01 g per one gram of the collagen solution, preferably 0.003 to 0.01 g per one gram of the collagen solution.

Organic solvent may be further added to the collagen solution to which the carbonate apatite is mixed. The organic solvent to be added is not particularly limited, provided that the organic solvent can decrease viscosity of the mixture. However, alcoholic organic solvent is preferable, and ethanol is most preferable. The organic solvent may be added to the collagen solvent before the carbonate apatite is mixed. A ratio of the organic solvent is generally 0.01 to 0.5 g per one gram of the collagen solution, preferably 0.1 to 0.3 g per one gram of the collagen solution. In addition, an amount of the organic solvent to be added is preferably an amount that adjusts viscosity of the mixture to within a range of 100 to 5000 mPa·s.

Freeze dehydration can be performed in such a manner that the mixture of the collagen and the carbonate apatite is put in an appropriate container or the like, and then is freeze-dried by using a commercially available freeze drier.

One of the methods for the sponge-like material that is formed from the complex of the carbonate apatite and collagen (hereinafter called "carbonate apatite-collagen sponge") to contain the SVVYGLR peptide (SEQ ID NO: 1), is to soak the carbonate apatite-collagen sponge obtained with the above described method into the SVVYGLR peptide (SEQ ID NO: 1) solution, so that the SVVYGLR peptide (SEQ ID NO: 1) is attached to a surface of the sponge. In this case, a concentration of the SVVYGLR peptide (SEQ ID NO: 1) solution is preferably 1 ng/ml to 10 µg/ml.

Further, as described in the section of MESENCHYMAL CELL PROLIFERATION PROMOTER, the carbonate apatite-collagen sponge containing the SVVYGLR peptide (SEQ ID NO: 1) can also be produced through the steps of: binding the SVVYGLR peptide (SEQ ID NO: 1) to the collagen (career protein) in advance, and producing the carbonate apatite-collagen sponge based on the foregoing method by using the collagen containing the SVVYGLR peptide (SEQ ID NO: 1).

The skeletal system biomaterial produced with the above described methods can be preferably used for regenerating bone marrow injured due to marrow disease or external injury, and for regenerating dental pulp after vital pulpectomy. That is, by implanting the skeletal system biomaterial according to the present invention to a damaged site to be repaired in bone marrow or to a site of the severed dental pulp, the bone marrow or the dental pulp can be regenerated and repaired.

[Method for Regenerating Bone Marrow Tissue or Dental Pulp Tissue]

A method according to the present invention for regenerating bone marrow tissue or dental pulp tissue may be selected from those using a skeletal system biomaterial according to the present invention. In the method, a carbonate apatite-collagen sponge containing a SVVYGLR peptide (SEQ ID NO: 1) is to be applied to a damaged site in bone marrow or a site of severed dental pulp, which are desired to be regenerated and/or repaired.

The embodiments discussed in the foregoing best mode for carrying out the invention and concrete examples set forth below serve solely to illustrate the technical details of the present invention, which should not be narrowly interpreted within the limits of such embodiments and concrete examples, but rather may be applied by a person skilled in the art in many variations within the spirit of the present invention, provided such variations do not exceed the scope of the patent claims set forth below.

Further, all the academic documents and patent documents stated in the description are invoked within the description as references.

EXAMPLES

Example 1

Effect Exerted on Proliferating Ability of Mesenchymal Cells by SVVYGLR Peptide (SEQ ID NO: 1)

An in vitro experiment was conducted to analyze how the SVVYGLR peptide (SEQ ID NO: 1) affected a proliferating ability of mesenchymal cells present in intercellular substances of bone marrow and dental pulp.

Purchased human bone marrow-derived mesenchymal stem cells (Cambrex BioScience Inc.) were used as the mesenchymal cells of the intercellular substance of bone marrow. Further, "dental pulp cells", the mesenchymal cells that constitute a main component of dental pulp tissue, were isolated from a lower incisor of a Sprague-Dawley rat (8-week old male) and cultured based on the method of Nakamura H et al. (J Dent Res. 84: 515-520: 2005), and used for the experiment.

These cells were seeded into a 96-well cell culture plate at a rate of 5,000 cells/well, and the number of cells under the presence of the SVVYGLR peptide (SEQ ID NO: 1) (0 to 100 ng/ml) was measured by using WST-1 Cell Counting Kit (DOJINDO LABORATORIES). A culture medium was replaced every other day.

The SVVYGLR peptide (SEQ ID NO: 1) was synthesized with a solid-phase synthesis by Fmoc method (solid-phase support: PEG-PS) by using a PSSM-8 peptide synthesizing apparatus (Shimazu Corporation). After a peptide chain was synthesized, a side chain protection was removed to separate off the peptide that is bound to resin. The obtained peptide was confirmed as a pure SVVYGLR peptide (SEQ ID NO: 1), by using HPLC (Shimazu Corporation).

Figure 1:
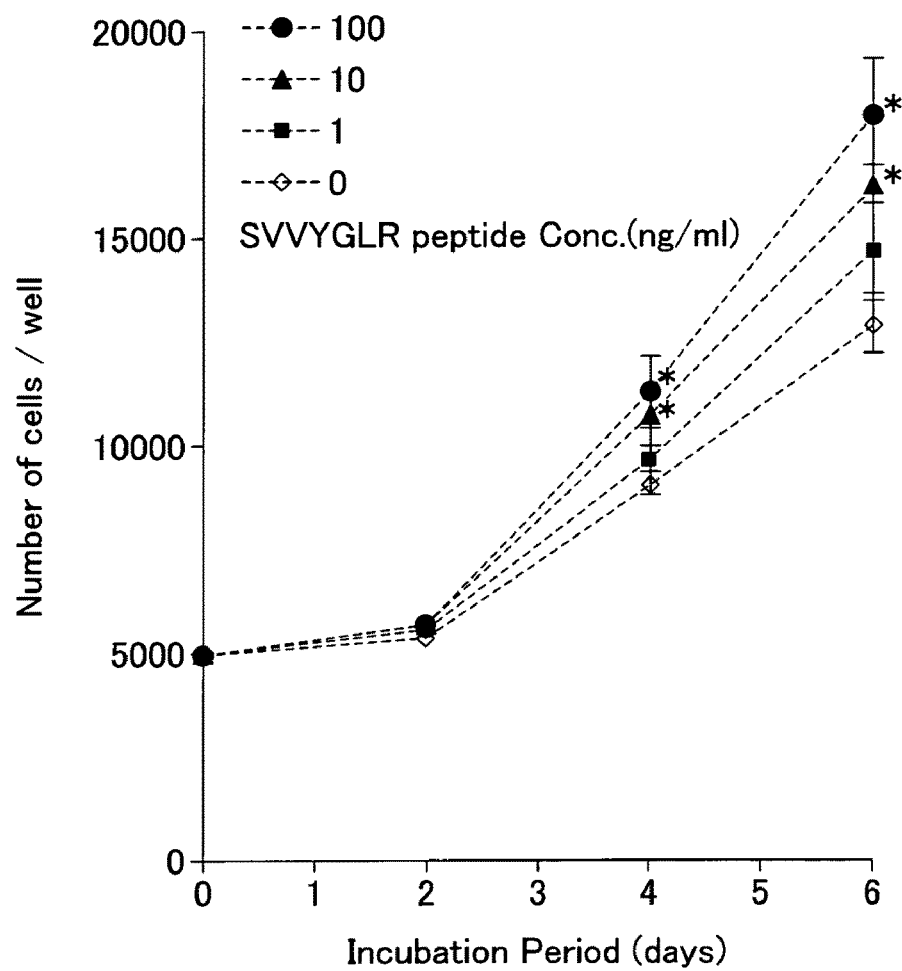
FIG. 1 is a graph showing a result of analyzing an effect exerted on proliferation of human marrow-derived mesenchymal stem cells by a SVVYGLR peptide (SEQ ID NO: 1).

FIG. 1 shows a result on the human marrow-derived mesenchymal stem cells. In FIG. 1, the number of samples in each group is n=6, and results are expressed as mean±SD. As obvious from FIG. 1, the number of the human marrow-derived mesenchymal stem cells cultured under the presence of the SVVYGLR peptide (SEQ ID NO: 1) (10 to 100 ng/ml) significantly increased on day-4 or later ($P<0.01$), compared to a control group cultured without the SVVYGLR peptide (SEQ ID NO: 1) (0 ng/ml).

Figure 2:
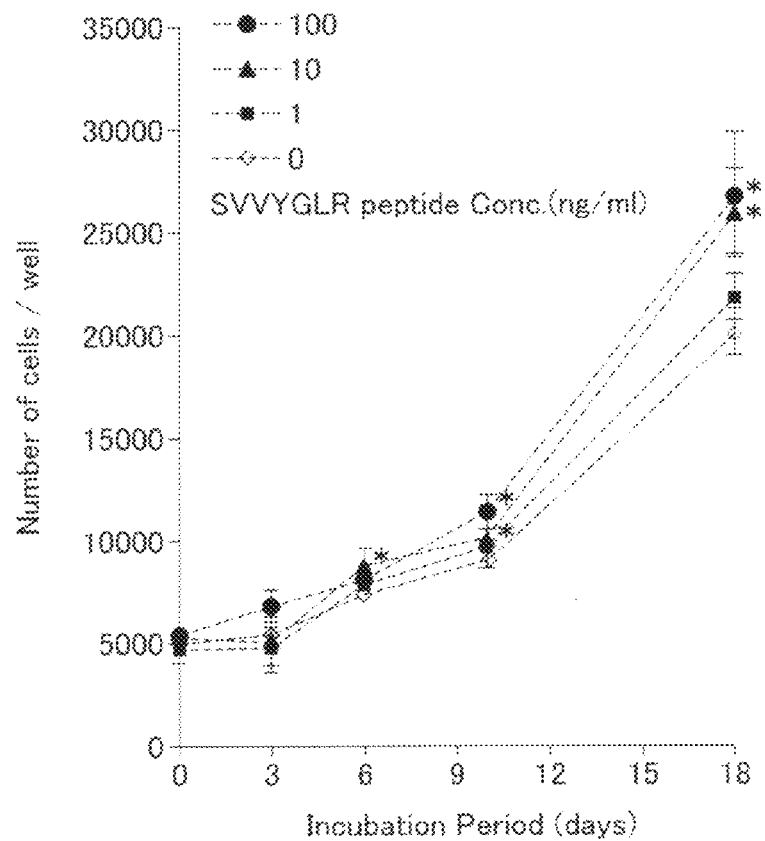
FIG. 2 is a graph showing a result of analyzing an effect exerted on proliferation of dental pulp cells by the SVVYGLR peptide (SEQ ID NO: 1).

FIG. 2 shows a result on the dental pulp cells. In FIG. 2, the number of samples in each group is n=6, and the result is expressed as mean±SD. As obvious from FIG. 2, the number of the dental pulp cells cultured under the presence of the SVVYGLR peptide (SEQ ID NO: 1) (10 to 100 ng/ml) significantly increased on day-10 or later ($P<0.01$), compared to a control group cultured without the SVVYGLR peptide (SEQ ID NO: 1) (0 ng/ml).

These results demonstrated that the SVVYGLR peptide (SEQ ID NO: 1) promotes proliferation of the human marrow-derived mesenchymal stem cells and dental pulp cells, density-dependently.

Example 2

Effect Exerted on Three-Dimensional Proliferation of Mesenchymal Cells by SVVYGLR Peptide (SEQ ID NO: 1)

A pellet culture experiment was conducted to analyze how the SVVYGLR peptide (SEQ ID NO: 1) affected the mesenchymal cells when the mesenchymal cells clump together three-dimensionally over a long time.

The mesenchymal cells were isolated from thigh bone marrow of a Sprague-Dawley rat (8-week old male), and cultured in a pellet culture with initial count of 50,000 cells based on the method of Tsutsumi S et al. (Biochem Biophys Res Commun. 288:413-419:2001). The incubation was carried out with a culture medium prepared in such a manner that dexamethasone (100 nM, Sigma-Aldrich), ascorbic acid (50 µg/ml, Sigma-Aldrich), ITS+ premix (100 times diluted, BD Biosciences), and recombinant human transforming growth factor-β1 (10 ng/ml, PeproTech EC) were added to α-MEM (high glucose: Nacalai Tesque, Inc). The SVVYGLR peptide (SEQ ID NO: 1) (100 ng/ml) was added to the culture medium and the pellet was incubated for 26 days. The culture medium was replaced every other day.

The pellet was collected and fixed in phosphate buffered 10% formalin solution for 3 hours at 4° C. After the pellet was washed with PBS (pH7.4), the pellet was soaked in the PBS of a culture plate and photographed under a phase contrast microscope. Planar dimensions of the pellet on a photographed image were measured by using an image analysis software ImageJ ver.1.33u (National Institute of health, USA).

Results are shown in FIGS. 3 and 4. (a) of FIG. 3 is a phase contrast microscope image of the pellet having the culture medium to which no SVVYGLR peptide (SEQ ID NO: 1) was added, and (b) of FIG. 3 is a phase contrast microscope image of the pellet having the culture medium to which the SVVYGLR peptide (SEQ ID NO: 1) was added. By comparing with both images, it is clearly understood that the pellet in (b) of FIG. 3 is larger in size. FIG. 4 is a graph showing measured values (μm2) of the planar dimensions of the pellet in the phase contrast microscope image. Three pellets from each group were measured, and mean value ±SD is shown in the graph. As obvious from FIG. 4, a pellet having the culture medium to which the SVVYGLR peptide (SEQ ID NO: 1) was added is 1.5 times larger in size than that of a control group.

Segments cut out from these pellets were stained toluidine blue. The observation showed that no toluidine blue staining was observed, and simple increase in the number of cells was observed. That is, it has been confirmed that an amount of extracellular matrix (acid mucopolysaccharide) produced within the pellet by the cells is not a cause of the increase in pellet size, but increased proliferation of cells themselves is the cause of the increase in the pellet size. The results suggested a possibility that the SVVYGLR peptide (SEQ ID NO: 1) promotes proliferation of the mesenchymal cells when the cells were cultured over a long time in the state of pellets.

Example 3

Producing Carbonate Apatite-Collagen Sponge Containing SVVYGLR Peptide (SEQ ID NO: 1)

Carbonate apatite was synthesized at 60±1□, pH7.4±0.2. First, 0.5 L of Ca(CH3COO)2H2O solution (100 mmol/L) and 0.5 L of NH4H2PO4 solution containing (NH4)2CO3 (60 mmol/L) were added to 1 L of acetic buffer (1.3 mol/L) under stirring. After being stirred for 3 hours, the mixture was allowed to stand for 24 hours at 25□. And then the mixture was filtered to isolate the carbonate apatite. The isolated carbonate apatite was washed with distilled water, and dried at 60□. In this way, the carbonate apatite was obtained.

An X-ray diffraction of the obtained synthetic carbon apatite was performed by using X-ray diffractometer (DX1, Shimazu Corporation). FIG. 5 shows an X-ray diffraction pattern of the synthetic carbonate apatite. Comparing this with a hydroxyapatite having a high-crystallized pattern, it is recognized that the synthetic carbonate apatite has a low-crystallization apatite pattern and is similar to a pattern of human bone.

Collagen solution used in this process was 0.5 wt % collagen solution (cow skin derived collagen, KOKEN CO., LTD), which had been treated with enzyme so as to minimize an antigenecity before use. The collagen solution was neutralized with NaOH (0.05N) and immediately after that, mixed with the 70% (w/w) carbonate apatite (dry weight). The gel was dispensed into a 96-well plate, frozen for 2 hours at −80° C., and then dried for 24 hours by using a freeze drier (Eyela). In order for the gel to obtain insolubility, the freeze-dried gel was exposed for 4 hours to an ultraviolet lamp (10 W, 253.7 nm) that was located 10 cm away from the gel. A cylindrical carbonate apatite-collagen sponge of 6 mm×10 mm in size was obtained.

(a) of FIG. 6 shows an image of the carbonate apatite-collagen sponge observed through a scanning electron microscope (S-4100 system, Hitachi. Ltd.). Similarly, (b) of FIG. 6 shows a three-dimensional image extracted by using an X-ray microcomputed tomography. For the X-ray microcomputed tomography, Micro CT 1072 (SkyScan) was used.

(a) and (b) of FIG. 6 showed that pores of approximately 50 to 300 μm in size extended to deep inside the sponge. A clotted carbonate apatite crystal was observed together with fibrous ribbons of collagen of the carbonate apatite-collagen sponge.

The carbonate apatite-collagen sponge containing the SVVYGLR peptide (SEQ ID NO: 1) was produced in such a manner that the carbonate apatite-collagen sponge was soaked into the SVVYGLR peptide (SEQ ID NO: 1) solution (100 ng/ml).

In addition to this, a carbonate apatite-collagen sponge containing the SVVYGLR peptide (SEQ ID NO: 1) was produced also through the steps of: cross-linking the SVVYGLR peptide (SEQ ID NO: 1) to the collagen, mixing the collagen containing the SVVYGLR peptide (SEQ ID NO: 1) with the carbonate apatite in accordance with the above method, and freeze-drying the mixture.

Specifically, the collagen containing the SVVYGLR peptide (SEQ ID NO: 1) was produced in such a manner described below. First, GMBS (bifunctional cross-linkers) of ten times the amount of the collagen was reacted with the collagen in PBS for 2 hours at 4□. Secondly, the unreacted GMBS were removed by using a gel filtration column. Thirdly, the SVVYGLR peptide (SEQ ID NO: 1) of equivalent amount of the collagen was reacted with the collagen for 5 hours at room temperature. Finally, the collagen was converted to acetate salt by substitution via a desalination column, for the collagen to be used in the form of acetate salt. In the obtained collagen containing the SVVYGLR peptide (SEQ ID NO: 1), a weight ratio of the SVVYGLR peptide (SEQ ID NO: 1) to the collagen was approximately 1:4.

Example 4

Implantation of Carbonate Apatite-Collagen Sponge Containing SVVYGLR Peptide (SEQ ID NO: 1)

A 4-week old SPF/VAF Crl;CD(SD) male rat (CHARLES RIVER LABORATORIES JAPAN INC.) was used. Under anesthesia of pentobarbital (50 mg/kg), a UV-irradiated carbonate apatite-collagen sponge containing the SVVYGLR peptide (SEQ ID NO: 1) was surgically inserted into bone marrow of shinbone of the rat. Specifically, a 3×7 mm hole was drilled on the shinbone in a way that the bone marrow was not exposed, and then the bone marrow was exposed by using a bone chisel. A room for locating a graft was made by taking out a bone marrow monolayer. In this process, a control group comprised a rat to which the carbonate apatite-collagen sponge containing no SVVYGLR peptide (SEQ ID NO: 1) was implanted.

A week later, the rat was euthanized, and the graft was enucleated together with surrounding tissues. Upon enucleation, the graft was embedded by an OTC compound (Tissue Tek), within acetone dry ice.

A polyclonal antibody (Dako) against factor VIII (von Willebrand factor) was used as a primary antibody. After the frozen section having a thickness of 6 μm was fixed in phosphate buffered 10% formalin solution for 10 minutes, the primary antibody diluted to 1:400 was put on top of the section and then the section was reacted for 14 hours at 4° C. The section was rinsed with Tris-Hci buffer solution containing 0.1% of tween-20, and then treated with a biotinylated anti-rabbit immunglobulin (Amersham) for 30 minutes at room temperature. After the rinse, alkaline phosphatase-labeled streptavidin (Dako) was reacted with the section. Alkaline phosphatase activity became visible within new fuchsin.

A nuclear of the section was counterstained with hematoxylin. In addition, another frozen section was stained with hematoxylin-eosin.

(a), (b), and (c) of FIG. 7 show a histological picture of the graft to which the carbonate apatite-collagen sponge containing the SVVYGLR peptide (SEQ ID NO: 1) was implanted. (b) of FIG. 7 is an enlarged image of X part of (a) of FIG. 7 and (c) of FIG. 7 is an enlarged image of Y part of (a) of FIG. 7. The X part is a carbonate apatite-collagen sponge region near a boundary with bone marrow, and the Y part is trabecular bone section.

In (b) of FIG. 7, as represented by a stained area of factor VIII indicated with an arrow, a large number of blood vessel figures that are formed from endocapillary cells positive for the factor VIII were clearly observed. In addition, infiltration of the endocapillary cells into the carbonate apatite-collagen sponge was recognized. Further, a large number of mesenchymal cells were observed inside the carbonate apatite-collagen sponge. In (c) of FIG. 7, Haversian canal that is formed from the endocapillary cells positive for the factor VIII was recognized in the trabecular bone.

It was confirmed that the implanted carbonate apatite-collagen sponge was not absorbed or dissolved within a week postoperatively, and existed as a madreporic body.

(a) and (b) of FIG. 8 show histological pictures of a control graft, to which the carbonate apatite-collagen sponge containing no SVVYGLR peptide (SEQ ID NO: 1) was implanted. (a) of FIG. 8 is an enlarged image of Z part of (a) of FIG. 8. The Z part is the carbonate apatite-collagen sponge region, near the boundary with the bone marrow.

In FIG. 8, few cells positive for the factor VIII were observed, and blood vessels were observed only around the boundary between the graft of (b) of FIG. 8 and the bone marrow. Further, few mesenchymal cells were observed inside the graft madreporic body.

Example 5

Effect Exerted on Adhesive Capacity of Mesenchymal Cells by SVVYGLR Peptide (SEQ ID NO: 1)

An effect that is exerted on adhesive capacity of the mesenchymal cells by the SVVYGLR peptide (SEQ ID NO: 1) was analyzed. The mesenchymal cells used in this example were: human marrow-derived mesenchymal stem cells (human mesenchymal stem cell for study: provided by RIKEN CELL BANK); human gingival fibroblasts (isolated from human gingival and cultured according to a publicly known method); and human periodontal ligament cells (normal human periodontal ligament fibroblast cells: purchased from Sanko Junyaku Co., Ltd).

A coating plate was produced through the steps of: adding the synthesized SVVYGLR peptide (SEQ ID NO: 1) (0 to 100 μg/ml) to a 96-well microplate for floating cells (ASAHI TECHNO GLASS CORPORATION) for culturing these cells, allowing the microplate to stand for 2 hours at 37□, and rinsing the microplate twice in phosphate buffer (PBS: Sigma Pharmaceuticals Ltd). The SVVYGLR peptide (SEQ ID NO: 1) was synthesized with the method described in example 1.

The human marrow-derived mesenchymal stem cells, human gingival fibroblasts, and human periodontal ligament cells, which were suspended in Dulbecco's Modified Eagle's Medium (DMEM: Nacalai Tesque, Inc.), were added to the coating plate coated with the SVVYGLR peptide (SEQ ID NO: 1), at a rate of 20,000 cells per well. The coating plate to which the cells are added was incubated for 30 minutes inside a CO2 incubator (5% CO2) at 37□ and rinsed twice with PBS, and then the unattached cells were removed.

The cells attached to the coating plate were stained with 0.1% crystal violet (Wako Chemicals USA. Inc) for minutes, and then rinsed three times with PBS. Twenty-percent TritonX (Sigma Pharmaceuticals Ltd) was added to each well, and 48 hours later, optical density of each well at a wavelength of 550 μm was measured (reference wavelength 630 μm) by using an optical density spectrometer (BioRad model 680).

FIGS. 9 to 11 show a result of evaluating the number of cells by each type of cells adhered to the coating plate. In FIGS. 9 to 11, the number of samples in each group is n=8, and the result is expressed as mean±SD. FIG. 9 shows a result on the human marrow-derived mesenchymal stem cells. As obvious from FIG. 9, the number of the human marrow-derived mesenchymal stem cells adhered to the plate coated with the SVVYGLR peptide (SEQ ID NO: 1) (0.01 to 100 μg/ml) has significantly increased density-dependently (P<0.01), compared to a control group in which the cells are adhered to the plate not coated with the SVVYGLR peptide (SEQ ID NO: 1) (0 μg/ml).

Further, FIGS. 10 and 11 show results on the human gingival fibroblasts and human periodontal ligament cells. As obvious from FIGS. 10 and 11, the number of the human gingival fibroblasts and human periodontal ligament cells adhered to the plate coated with the SVVYGLR peptide (SEQ ID NO: 1) (0.01 to 100 μg/ml) has significantly increased density-dependently (P<0.01), compared to a control group in which the cells are adhered to the plate not coated with the SVVYGLR peptide (SEQ ID NO: 1) (0 μg/ml).

These results have proved that the SVVYGLR peptide (SEQ ID NO: 1) density-dependently promotes the adhesion of the human marrow-derived mesenchymal stem cells, human gingival fibroblasts, and human periodontal ligament cells. The results also suggest that by coating a biomaterial like the foregoing carbonate apatite-collagen sponge with the SVVYGLR peptide (SEQ ID NO: 1) and implanting the coated biomaterial into the living organism, the adhesion of the mesenchymal cells inside the living organism can be promoted.

The angiogenic inducement and mesenchymal cell proliferation promoter of the present invention can be effectively used for repairing mesenchymal tissues. Especially, it is possible to provide a very useful tool for regenerating a dental pulp tissue after marrow disease, vital pulpectomy, or the like.

In addition, since an active ingredient of the mesenchymal cell proliferation promoter of the present invention is a peptide comprising seven amino acids, the mesenchymal cell proliferation promoter has such an advantage that fewer side effects are expected than those containing proteins of large molar weight in terms of antigenecity, and so it is safe and easy to be metabolized. Further, although the proteins have such problems as infections and unexpected side effects because of the necessity for the proteins to be produced as recombination protein or protein extract, the peptide has an established high-efficient synthesis method, so the peptide is preferable also in terms of cost of manufacturing and safety.

The present invention allows for improvement in people's QOL and reduction of medical costs.

The embodiments and concrete examples of implementation discussed in the foregoing detailed explanation serve solely to illustrate the technical details of the present invention, which should not be narrowly interpreted within the limits of such embodiments and concrete examples, but rather may be applied in many variations within the spirit of the present invention, provided such variations do not exceed the scope of the patent claims set forth below.

INDUSTRIAL APPLICABILITY

The present invention is very useful as artificial bone marrow or artificial dental pulp, and is applicable in pharmaceutical industry and medical equipment industry.

The invention claimed is:

1. A method for regenerating a bone marrow tissue or a dental pulp tissue, comprising:
   administering a regeneration promoter to a damaged area or a defective area of the bone marrow tissue or the dental pulp tissue, the regeneration promoter including a peptide as an active ingredient, wherein the peptide consists of SEQ ID NO: 1.

* * * * *

UNITED STATES PATENT AND TRADEMARK OFFICE
Certificate

Patent No. 8,222,216 B2　　　　　　　　　　　　　　　　　　　　　　　　Patented: July 17, 2012

On petition requesting issuance of a certificate for correction of inventorship pursuant to 35 U.S.C. 256, it has been found that the above identified patent, through error and without any deceptive intent, improperly sets forth the inventorship.
　Accordingly, it is hereby certified that the correct inventorship of this patent is: Yoshinosuke Hamada, Suita (JP); Nariaki Matsuura, Suita (JP); Hiroshi Egusa, Suita (JP); Yoshitoshi Kaneda, Suita (JP); Masayuki Okazaki, Hiroshima (JP); and Hirofumi Yatani, Suita (JP).

Signed and Sealed this Twenty-ninth Day of January 2013.

<div style="text-align:right">CECILIA TSANG<br>
*Supervisory Patent Examiner*<br>
Art Unit 1654<br>
Technology Center 1600</div>